United States Patent
Scheinberg et al.

(10) Patent No.: US 11,660,357 B2
(45) Date of Patent: May 30, 2023

(54) ONE-STEP LABELING OF ANTIBODIES TO HIGH SPECIFIC ACTIVITY WITH ACTINIUM-225

(71) Applicants: David A. Scheinberg, New York, NY (US); Peter M. Smith-Jones, Port Jefferson, NY (US); Michael R. McDevitt, Bronx, NY (US); William F. Maguire, Colombia, MD (US)

(72) Inventors: David A. Scheinberg, New York, NY (US); Peter M. Smith-Jones, Port Jefferson, NY (US); Michael R. McDevitt, Bronx, NY (US); William F. Maguire, Colombia, MD (US)

( * ) Notice: Subject to any disclaimer, the term of this patent is extended or adjusted under 35 U.S.C. 154(b) by 266 days.

(21) Appl. No.: 15/311,721

(22) PCT Filed: May 18, 2015

(86) PCT No.: PCT/US2015/031326
§ 371 (c)(1),
(2) Date: Nov. 16, 2016

(87) PCT Pub. No.: WO2015/176056
PCT Pub. Date: Nov. 19, 2015

(65) Prior Publication Data
US 2017/0112951 A1    Apr. 27, 2017

Related U.S. Application Data

(60) Provisional application No. 61/994,318, filed on May 16, 2014, provisional application No. 62/131,322, filed on Mar. 11, 2015.

(51) Int. Cl.
*A61K 51/10* (2006.01)
*C07K 16/28* (2006.01)
*C07K 16/32* (2006.01)
*A61K 39/00* (2006.01)

(52) U.S. Cl.
CPC ...... *A61K 51/1096* (2013.01); *A61K 51/1027* (2013.01); *A61K 51/1045* (2013.01); *C07K 16/2803* (2013.01); *C07K 16/2887* (2013.01); *C07K 16/32* (2013.01); *A61K 2039/505* (2013.01)

(58) Field of Classification Search
CPC ............ A61K 51/1096; A61K 51/1045; A61K 2039/505; C07K 16/2803; C07K 16/2887; C07K 16/32
USPC ........................................................ 424/1.53
See application file for complete search history.

(56) References Cited

U.S. PATENT DOCUMENTS

2011/0117014 A1* 5/2011 Norenberg .......... A61K 31/4178
424/1.65
2012/0009121 A1* 1/2012 Pomper ................ C07D 209/14
424/1.11

OTHER PUBLICATIONS

Miederer et al. Clin. Cancer Res. 2008, 14, 3555-3561.*
Lewis et al. Bioconjugate Chem. 1994, 5, 565-576.*
Forrer et al. Eur. J. Nucl. Med. Mol. Imaging 2009, 36, 1443-1452.*
Reilly Cancer Biother. Radiopharm. 2004, 669-672.*

* cited by examiner

*Primary Examiner* — Michael G. Hartley
*Assistant Examiner* — Sean R Donohue
(74) *Attorney, Agent, or Firm* — Benjamin Aaron Adler

(57) ABSTRACT

Provided herein is a one-step method for chelating actinium-225 to a construct comprising a chelator linked to a biomolecule, such as, an antibody or monoclonal antibody, via a bifunctional ligand in, for example, a 3-arm configuration. Also provided are methods for increasing the radiochemical yield of an actinium-225-chelant-biomolecule complex and for producing a high specific activity actinium-225 complex. The chelation is performed at a physiological temperature, about 37° C. Also provided are high specific activity actinium-225 complexes, that is, actinium-225 chelated to the chelator-biomolecule construct and pharmaceutical compositions thereof. Further provided are methods of treating a neoplastic disease or disorder with the actinium-225 complexes.

9 Claims, 12 Drawing Sheets

DTPA-HuM195

CHX-A"-DTPA-HuM195

1: Untreated (vehicle)
2: Cold ESK D265A
3: ESKM @ 50 µg
4: Low SA Ac-ESK @ 30 nCi
5: Ac-Iso @ 30 nCi
6: Ac-ESK @ 30 nCi
7: Ac-Iso @ 60 nCi
8: Ac-ESK @ 60 nCi (n = 4)



ONE-STEP LABELING OF ANTIBODIES TO HIGH SPECIFIC ACTIVITY WITH ACTINIUM-225

CROSS-REFERENCE TO RELATED APPLICATIONS

This application is a national stage application under 35 U.S.C. § 371 of international patent application PCT/US2015/031326, filed May 18, 2015, which claims benefit of priority under 35 U.S.C. § 119(e) to provisional application U.S. Ser. No. 62/131,322, filed Mar. 11, 2015, and to provisional application U.S. Ser. No. 61/994,318, filed May 16, 2014, now abandoned, the entirety of all of which are hereby incorporated by reference.

FEDERAL FUNDING LEGEND

This invention was made with government support under Grant Numbers CA023766, CA055349 and GM007739 awarded by the National Institutes of Health. The government has certain rights in the invention.

BACKGROUND OF THE INVENTION

Field of the Invention

The present invention relates generally to the field of radioimmunotherapy and chelation chemistry. More specifically, the present invention relates to a one-step method for chelating actinium-225 to a biomolecule construct at physiological temperature and uses for the actinium-225 complex so produced.

Description of the Related Art

Alpha-particle-emitting radionuclides are promising agents for anticancer therapy, as evidenced by the recent FDA approval of $^{223}$Ra (Xofigo) for castration-resistant prostate cancer with bone metastases (1). Because of the high energy (5-8 MeV) and short path length (50-80 microns) of alpha particles, they have the potential to effectively and selectively target single cells, residual disease, and micrometastatic lesions. The alpha-particle-generator actinium-225 ($^{225}$Ac) has a 10-day half-life, which is well suited to the time needed for radiolabeling, injection, and tumor targeting; and releases 4 net alpha particles per atom of $^{225}$AC, which delivers massive toxicity to target cells (2).

Early work with $^{225}$AC was limited by difficulty attaching it to targeting vehicles such as peptides and monoclonal antibodies, the low specific activity achievable by the products, and the lack of a cost-effective labeling strategy. Various chelators were investigated, with many failing to chelate the metal at all and others appearing to radiolabel but then releasing actinium-225 when subjected to serum challenge (3-5). Stable labeling with the chelator 1,4,7,10-tetraazacyclododecane-1,4,7,10-tetraacetic acid (DOTA) was previously achieved using a procedure in two chemical steps that was designed to minimize radiolysis and maximize kinetic stability of the products (4,6). This procedure has since been used as a standard in a number of successful preclinical studies (7-9) and is currently in human clinical trials in the form of $^{225}$Ac-HuM195 to treat advanced myeloid leukemias.

A major drawback to the two-step labeling approach is that approximately 90% of the input actinium is conjugated to nonreactive forms of DOTA in the first step of the procedure and is consequently discarded. Because actinium-225 is a rare and expensive isotope, a more efficient procedure for preparing actinium-antibody constructs is necessary to promote the more widespread use of these agents. Additionally, the low specific activity currently available limits the type of cellular targets that can be attacked. The direct one-step labeling of pre-formed antibody-DOTA constructs is a potential solution to the above problems but was previously thought to be infeasible at temperatures low enough to be compatible with monoclonal antibodies (4,6). One-step labelings of peptide-DOTA constructs with actinium-225 have been reported (10-11), but they were carried out at temperatures of 70 degrees Celsius or higher.

Thus, there is a recognized need in the art for a more efficient actinium-225 chelation process. Particularly, the prior art is deficient in a one-step method carried out under physiological temperature for chelating actinium-225 to a biomolecule-chelator construct that produces a complex with a higher radiochemical yield and specific activity. The present invention fulfills this longstanding need and desire in the art.

SUMMARY OF THE INVENTION

The present invention is directed to a one-step chelation process for actinium-225. The process comprises chelating, under physiological conditions, actinium-225 to a chelator construct comprising a bifunctional ligand conjugated to said chelator in a 3-arm configuration and covalently linking a biomolecule thereto.

The present invention also is directed to an actinium-225-chelant-biomolecule complex produced by the chelation process described herein.

The present invention is further directed to a pharmaceutical composition comprising the actinium-225-chelant-antibody complex described herein and a pharmaceutically acceptable carrier.

The present invention is directed further still to a method for treating a neoplastic disease or disorder in a subject in need of such treatment. The method comprises administering a pharmacologically effective dose of the pharmaceutical composition described herein. In the method the biomolecule comprises a monoclonal antibody for targeting cells associated with the neoplastic disease or disorder such that, upon targeting, alpha particles from the actinium-225 and daughters thereof are delivered to the targeted cells and cause a cytotoxic effect thereto, thereby treating the neoplastic disease or disorder.

The present invention is directed further still to a method for inducing cytotoxicity in a cell associated with a neoplastic disease or disorder. The method comprises contacting the cell with the actinium-225-chelant-biomolecule complex described herein. The biomolecule targets the cell such that delivery of alpha particles emitted from the actinium-225 and daughters thereof to the cell induces cytotoxicity in the cell.

The present invention is directed further still to a method for increasing the radiochemical yield of an actinium-225-chelant-biomolecule complex. The method comprises conjugating a chelator to a biomolecule via a bifunctional ligand in a 3-arm configuration to form a chelator-biomolecule construct. An actinium-225 is chelated to the chelator-biomolecule construct to form an actinium-225-chelant-biomolecule complex where the one-step radiolabeling substantially or markedly decreases the amount of actinium-225 lost in the reaction whereby the radiochemical yield of the modified reaction is greatly increased.

The present invention is directed further still to a method for producing a high specific activity actinium-225-DOTA-biomolecule complex. The method comprises chelating at a physiological temperature actinium-225 to a DOTA-biomolecule construct comprising a bifunctional ligand conjugating the biomolecule to the DOTA in a 3-arm or a 4-arm configuration. The method at physiological temperature enables an increase in the activity incorporated onto the biomolecule, thereby producing the high specific activity actinium-225 complex.

The present invention is directed further still to a high-specific activity actinium-225-chelant-biomolecule complex or a pharmaceutical composition thereof produced by the methods described herein.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1A depicts the synthesis of 3-arm antibody constructs. FIG. 1B depicts the synthesis of 4-arm antibody constructs. FIG. 1C depicts the synthesis of control constructs.

FIG. 2A shows radiolabeling conditions. FIG. 2B shows the time course of labeling at different temperatures as assayed by iTLC.

FIG. 3A is an iTLC assay in vitro to determine percent actinium on protein. FIG. 3B is an assay of protein G binding of serum harvested from female Balb/c mice at specified timepoints. T=0 is uninjected material. All data are ±SD, n=3 per point.

FIG. 5A is a detailed representation of therapy with 15 nCi at day 26 post-tumor-injection. FIG. 5B is a detailed representation of therapy with 30 nCi at day 26 post-tumor-injection. FIG. 5C: Tumor growth curves plotted on a log scale.

DETAILED DESCRIPTION OF THE INVENTION

Figure 1A:
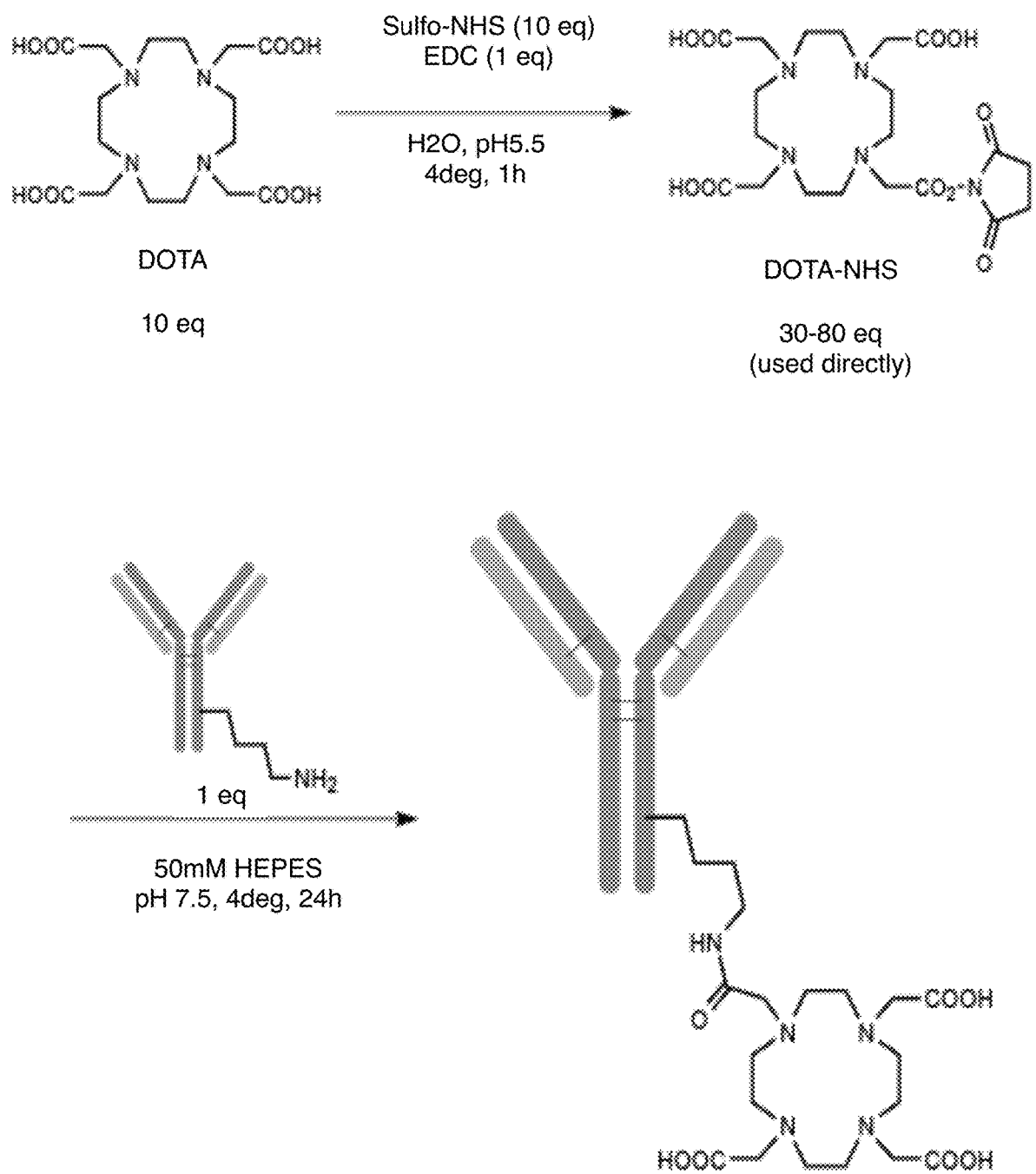
FIGS. 1A-1C show antibody-chelate constructs for one-step labeling.

As used herein, the term, "a" or "an" may mean one or more. As used herein in the claim(s), when used in conjunction with the word "comprising", the words "a" or "an" may mean one or more than one. Some embodiments of the invention may consist of or consist essentially of one or more elements, method steps, and/or methods of the invention. It is contemplated that any method, compound, composition, or device described herein can be implemented with respect to any other device, compound, composition, or method described herein.

As used herein, the term "or" in the claims refers to "and/or" unless explicitly indicated to refer to alternatives only or the alternatives are mutually exclusive, although the disclosure supports a definition that refers to only alternatives and "and/or".

As used herein, the term "about" refers to a numeric value, including, for example, whole numbers, fractions, and percentages, whether or not explicitly indicated. The term "about" generally refers to a range of numerical values, e.g., +/−5-10% of the recited value, that one of ordinary skill in the art would consider equivalent to the recited value, e.g., having the same function or result. In some instances, the term "about" may include numerical values that are rounded to the nearest significant figure.

As used herein, the terms "chelator" or "chelating agent" are interchangeable and refers to a chemical compound to which a radiometal, such as actinium-225, or metal can be chelated via coordinate bonding. Preferably, the chelator comprises a heterocyclic ring.

As used herein, the terms "chelant" or "chelate" are interchangeable and refers to the chelator or chelating agent bonded to the radiometal or metal.

As used herein, the term "construct" refers to a chelator or chelating agent covalently linked to a biomolecule via a bifunctional ligand.

As used herein, the term "complex" refers to a chelant-linker-biomolecule configuration, for example, actinium-225-chelator-biomolecule.

As used herein, the term "contacting" refers to any method suitable for delivering an actinium-225 radiometal or the complex comprising the same into contact with a target cell, tissue or vasculature. In vitro or ex vivo this is achieved by exposing the target cell, tissue or vasculature to the actinium-225 radiometal or the complex in a suitable medium. For in vivo applications, any known method of administration is suitable as described herein.

As used herein, the terms "treating" or "treatment" includes prophylactic and/or therapeutic treatment as well as alleviation of ongoing or intermittent symptoms occurring in a neoplastic disease or disorder, such as, a primary cancer or a metastatic cancer, a benign tumor and the vasculature associated therewith.

As used herein, the term "subject" refers to any target of a treatment with the Actinium-225-biomolecule complex described herein, preferably a human, more preferably a human, although any mammal may be treated.

In one embodiment of the present invention there is provided a one-step chelation process for actinium-225, comprising chelating, under physiological conditions, actinium-225 to a chelator construct comprising a bifunctional ligand conjugated to said chelator in a 3-arm configuration and covalently linking a biomolecule thereto. In this embodiment, the physiological conditions may comprise a physiological temperature of about 37° C. Preferably, in this embodiment, the radiochemical yield of the process may be about 50% to about 85%. In addition, the process may produce actinium-225 chelated at a high specific activity of about 0.7 Ci/g to about 3.5 Ci/g.

In this embodiment, the chelator construct may comprise a bifunctional ligand covalently linked to a biomolecule. Particularly, the chelator may be 1,4,7,10-tetraazacyclododecane-1,4,7,10-tetraacetic acid (DOTA). Representative examples of the attachment moiety on the bifunctional ligand include but are not limited to benzyl-isothiocyanate, which forms a "four-arm" DOTA-biomolecule construct, and N-hydroxysuccinimide, which forms a "three-arm" DOTA-biomolecule complex. Furthermore, representative examples of the biomolecule include but are not limited to an antibody, a monoclonal antibody, a growth factor, a cytokine, a peptide, a ligand, or a chemical.

In another embodiment of the present invention, there is provided an actinium-225-chelant-biomolecule complex produced by the chelation process as described supra. In this embodiment, the complex may have a high specific activity of about 0.7 Ci/g to about 3.5 Ci/g. Representative actinium-225-chelant-biomolecule complexes include but are not limited to an actinium-225-DOTA-antibody complex or an actinium-225-DTPA-antibody complex.

In a related embodiment, the present invention provides a pharmaceutical composition comprising the actinium-225-chelant-antibody complex described supra and a pharmaceutically acceptable carrier.

In yet another embodiment of the present invention, there is provided a method for treating a neoplastic disease or disorder in a subject in need of such treatment comprising the steps of administering a pharmacologically effective dose of the pharmaceutical composition described supra; wherein the biomolecule comprises a monoclonal antibody for targeting cells associated with the neoplastic disease or disorder such that, upon targeting, alpha particles from the actinium-225 and daughters thereof are delivered to the targeted cells and cause a cytotoxic effect thereto, thereby treating the neoplastic disease or disorder. In this embodiment, representative examples of a neoplastic disease or disorder include but are not limited to a disseminated cancer, a solid tumor cancer, a hypertrophy, a coronary disease, or a vascular occlusive disease or is associated with an inflammatory cell, an infected cell, a microbe or virus.

In yet another embodiment of the present invention, there is provided a method for inducing cytotoxicity in a cell associated with a neoplastic disease or disorder, comprising contacting the cell with the actinium-225-chelant-biomolecule complex as described supra, wherein the biomolecule targets the cell such that delivery of alpha particles emitted from the actinium-225 and daughters thereof to the cell induces cytotoxicity in the cell. In this embodiment, representative examples of a cell may be associated with a cancer, a hypertrophic tissue, a tumor vasculature or a coronary vasculature. Alternatively, the cell may be an inflammatory cell, an infected cell, a microbe or a virus.

In yet another embodiment of the present invention, there is provided a method for increasing the radiochemical yield of an actinium-225-chelant-biomolecule complex, comprising conjugating a chelator to a biomolecule via a bifunctional ligand in a 3-arm configuration to form a chelator-biomolecule construct; and chelating actinium-225 to the chelator-biomolecule construct to form an actinium-225-chelant-biomolecule complex, where the one-step radiolabeling decreases the amount of actinium-225 lost in the reaction, thereby increasing the radiochemical yield. In this embodiment the radiochemical yield may be about 50% to about 85%. The physiological temperature may be about 37° C. In addition, the complex may be an actinium-225-DOTA-antibody complex. Further still, the complex may have a high specific activity of about 0.7 Ci/g to about 3.5 Ci/g.

In yet another embodiment of the present invention, there is provided a method for producing a high specific activity actinium-225-DOTA-biomolecule complex, comprising chelating at a physiological temperature actinium-225 to a DOTA-biomolecule construct comprising a bifunctional ligand conjugating the biomolecule to the DOTA in a 3-arm or a 4-arm configuration, where the physiological temperature enabling an increase in the activity incorporated onto the biomolecule, thereby producing the high specific activity actinium-225 complex. In this embodiment, the high specific activity is about 0.7 Ci/g to about 3.5 Ci/g. Preferably, a radiochemical yield of said complex is about 50% to about 85%. The biomolecule and the bifunctional ligand are as described supra.

In yet another embodiment of the present invention, there is provided a high-specific activity actinium-225-chelant-biomolecule complex or a pharmaceutical composition thereof produced by the method at physiological temperatures as described supra.

Provided herein is an efficient, one-step chelating method that produces stable, therapeutically active conjugates of actinium-225 at high specific activity under physiological conditions. Generally, a chelator-biomolecule construct can be labeled to a wide range of specific activities in one chemical step at about 37° C. with radiochemical yields about ten-fold higher and specific activities about 30-fold higher than produced by known methods. The actinium-225-chelant-biomolecule complexes retain immunoreactivity and are stable in serum in vitro and in vivo.

The one-step chelating method produces actinium-225 complexes with a radiochemical yield of about 50% to about 85%. The resultant specific activity may be about 0.7 Ci/g to about 3.5 Ci/g. All of the chelators present in the 1-step procedure are already attached to the biomolecule, such that the amount of actinium that can be chelated to the construct at 37° C. is only limited by the capacity of the biomolecule construct.

The one-step procedure has pharmaceutical and regulatory advantages over previous two-step procedures. Chelator-biomolecute constructs can be prepared in a central location, qualified, and stored indefinitely. The end user is only responsible for adding actinium-225 and purifying the product, and the specific activity can be adjusted simply by adjusting the amount of actinium-225 added to the construct.

The chelator comprising the chelator-biomolecule construct must be able to chelate an alpha emitting radionuclide, particularly, the actinium-225 radionuclide and may be, for example, 1,4,7,10-tetraazacyclododecane-1,4,7,10-tetraacetic acid (DOTA). The biomolecule may be linked to the chelator in a "3-arm" or a "4-arm" configuration with a bifunctional ligand such as, preferably, a N-hydroxysuccinimide moiety or, alternatively, a benzyl-isothiocyanate moiety. The biomolecule may be an antibody, for example, a monoclonal antibody, such as, but not limited to, HuM195, Rituximab, J591, B4, 3F8, and ESK or may be a growth factor, a cytokine, or a peptide, or the chelator may be conjugated to another cell targeting vehicle or biomolecule such as a ligand or a chemical.

Further provided are actinium-225-chelant-biomolecule complexes produced by the methods described herein. Preferably, the complex is an actinium-225-DOTA-antibody complex in a "4-arm" or "3-arm" configuration. The actinium-225 complexes may be formulated as pharmaceutical compositions in a pharmaceutically or physiologically acceptable carrier, excipient or diluent suitable for a chosen route of administration. A preferred route of administration to a subject is intravenously. Such carriers, excipients, and diluents are well-known in the art and available to an end-user for the one-step preparation and purification of the actinium-225 complexes.

Thus, the present inventions provides methods for treating a neoplastic disease or disorder or symptoms associated therewith. The biomolecule in the actinium-225 complexes may comprise a targeting moiety, such as, an antibody, monoclonal antibody or other peptide that targets a cell, tissue or vasculature associated with the neoplastic disease or disorder. Without being limiting, the cells, tissue or vasculature may comprise or be associated with a disseminated or a solid cancer, for example, lymphoma, leukemia, prostate cancer, lymphoma, leukemia, neuroblastomas, breast cancer, and ovarian cancer. Alternatively, the cells, tissue or vasculature may comprise or be associated with a benign neoplasm, a hypertrophic disease or disorder, such as prostatic hypertrophy, a coronary disease, or a vascular occlusive disease. Moreover, representative examples of a cell include but are not limited to an inflammatory cell, an infected cell, a microbe, or a virus. Upon delivering to or contacting the one or more of the targets with a pharmacologically or chemotherapeutically effective dose, the actinium-225 is positioned to deliver four net alpha particles to the target(s) for a therapeutic or chemotherapeutic effect.

One of ordinary skill in the art is well-able to determine a therapeutic regimen utilizing the high specific activity Actinium-225-chelant-biomolecule complexes produced by the one-step radiolabeling process disclosed herein or pharmaceutical compositions thereof. Such a therapeutic regimen would be based on the subject's health, the progression or remission of the disease, the route of administration and the formulation used. The actinium-225 complexes and pharmaceutical compositions thereof may be administered one or more times to achieve a therapeutic or chemotherapeutic effect. It is well within the skill of an artisan to determine dosage or whether a suitable dosage comprises a single administered dose or multiple administered doses. As such it is recognized that the optimal quantity and spacing of individual dosages of the complexes or pharmaceutical compositions of the present invention are determined by the nature and extent of the condition being treated and that such optimums can be determined by conventional techniques.

The following examples are given for the purpose of illustrating various embodiments of the invention and are not meant to limit the present invention in any fashion.

Example 1

Materials and Methods
Radionuclides, Reagents, and Monoclonal Antibodies
Actinium-225 was received from Oak Ridge National Laboratory as a nitrate residue, which was dissolved in 0.2M Optima grade HCl (Fisher Scientific) prior to use. Actinium-225 activity was measured using a CRC-15R radioisotope calibrator (Capintec, Inc) set at 775 and the displayed activity value was multiplied by 5. The parent Actinium-225 was measured when it was in secular equilibrium with its daughters, at least 6 hours and typically the next day after sample collection.

The chelating agent 1,4,7,10-tetraazacyclododecane-1,4,7,10-tetraacetic acid (DOTA) and the bifunctional ligands 2-(4-isothiocyanatobenzyl)-1,4,7,10-tetra azacyclododecane-1,4,7,10-tetraacetic acid, (p-SCN-Bn-DOTA); and 2-(4-isothiocyanatobenzyl)-diethylenetriaminepentaacetic acid, (p-SCN-Bn-DTPA) were obtained from Macrocyclics. The structures of the DOTA chelating agents and controls are shown in FIG. 1.

Chemicals used in the conjugation, radiolabeling, and purification steps were American Chemical Society (ACS) reagent grade or better. Water and buffers were rendered metal-free by passing them through a column of Chelex-100 resin, 200-400 mesh (Bio-Rad Laboratories, Inc) and were sterile filtered through a 0.22- or 0.45-μM filter device.

The monoclonal antibodies used were HuM195/Lintuzumab/anti-CD33 (Sloan-Kettering), Rituximab/anti-CD20 (Genentech), and ESK/anti-WT1 (Sloan-Kettering/Eureka Therapeutics). The preformed CHX-A"-DTPA HuM195 construct was prepared previously (TSI Washington) and used without further modification.

Synthesis, Purification, and Quality Control of Antibody-Chelate Constructs

The conjugation and radiolabeling procedures were carried out using sterile and pyrogen-free plasticware (Corning, Inc, and Fisher Scientific) and metal-free pipette tips (Bio-Rad Laboratories, Inc). Monoclonal antibodies (5-10 mg in 0.5-2 ml PBS) were transferred to 15 ml Vivaspin Centrifugal Concentrators with a 10,000 kD molecular weight cutoff (Sartorius Corporation). To render the antibodies metal-free, the Vivaspins were filled to 15 ml with 20 mM (1%) DTPA and allowed to sit at 4 degrees overnight. The antibody buffer was then exchanged to 50 mM HEPES pH 7.5 by three complete rounds of concentration and subsequent dilution. The products were transferred to 1.8 ml Nunc cryovials (Fisher Scientific) at a concentration of >1 mg/ml and subjected to reaction conditions as detailed below.

To form the 3-arm DOTA constructs, DOTA NHS ester was first generated in situ using a standard procedure (12-13). In a typical reaction, DOTA (65.6 mg, 10 eq) and Sulfo-NHS (27.79 mg, 10 eq) were dissolved in 600 ml of metal-free water at 4 degrees Celsius. A 10 mg aliquot of EDC (Thermo Scientific) was dissolved in 200 ml of metal-free water, and 49.1 ml (2.45 mg, 1 eq) of this solution was added to the DOTA/Sulfo-NHS solution. The pH of the reaction was adjusted to ~5.7 by repeated additions of metal-free sodium hydroxide (NaOH), and the reaction was allowed to proceed for 30 minutes at 4 degrees Celsius. An appropriate amount of activated ester (30-80 eq) was added to the antibody (1 eq) in HEPES buffer at 4 degrees, and the pH was re-adjusted to 7.5 by adding NaOH. The reaction was allowed to proceed for 24 h at 4 degrees. The resulting product was purified via buffer exchange to 20 mM NaAc, 150 mM NaCl through multiple passes through a Vivaspin 15 as detailed before.

For formation of the 4-arm DOTA construct and DTPA construct, p-SCN-Bn-DOTA (20-30 eq) dissolved in water (40 mg/ml solution) was added to metal-free antibody (1 eq) in HEPES buffer, prepared via centrifugal concentration as described above. The pH was adjusted to 8.5 by adding NaOH. The reaction was allowed to proceed at room temperature for 12 h, and the product was purified via buffer exchange to 20 mM NaAc, 150 mM NaCl through multiple passes through a Vivaspin 15 centrifugal concentrator.

The protein concentration of the product constructs was determined using the Bio-Rad DC assay (Bio-Rad Laboratories, Inc). The average number of chelates per antibody was measured using the lead-arsenazo spectrophotometric method (14). For the 4-arm DOTA construct and the DTPA construct, the free ligands DOTA and DTPA were used to generate the standard curve. For the 3-arm DOTA construct, a three-arm DOTA-maleimide construct obtained from Macrocyclics was used as a standard.

Radiolabeling Procedures

The two-step radiolabeling procedure was carried out as previously reported (4). In a typical one-step procedure, $^{225}$Ac-nitrate dissolved in 0.2M HCl (3.7 MBq, 100 mCi) was added to a 1.0 ml Nunc vial and the activity was determined exactly using a dose calibrator. To this were added 2M tetramethyl ammonium acetate (TMAA) buffer (25 ml), 150 g/l L-ascorbic acid (10 ml), and the appropriate antibody construct (100 mg). pH of the reaction was determined by spotting 1 ul of the reaction mixture onto Hydrion pH paper range 5.0-9.0 (Sigma-Aldrich); pH of a typical reaction was 5.8. The reaction was transferred to a water bath displaying 37.0 degrees Celsius, and the reaction was allowed to proceed for 2 hours unless specifically noted. After this a small aliquot was spotted on an instant thin layer chromatography-silica gel (iTLC-SG) paper to determine the extent of incorporation of actinium onto protein. The reaction was then quenched with 50 mM DTPA (20 ml) and purified using an Econo-Pac 10 DG desalting column (Bio-Rad) that had been equilibrated previously with 1% Human Serum Albumin (HSA). The product was eluted in approximately 2 ml of 1% HSA and was spotted onto iTLC-SG paper to determine the radiochemical purity.

For the control constructs, the CHX-A"-DTPA construct was radiolabeled and purified with the one-step procedure. For both the DTPA construct and the unmodified antibody, reactions were not quenched or purified since this would remove a large portion of the free 225Ac. Rather they were diluted to an approximate final volume of 2 ml with 1% HSA.

Animal Studies

Female Balb/C mice aged 6-10 weeks were obtained from NCI-Frederick or Taconic Labs for the biodistribution studies in healthy animals. For the therapy studies, male Nod.Cg-Prkdc$^{scid}$-Il2rg$^{tm1Wjl}$/SzJ (Nod scid gamma or NSG) mice aged 9 weeks were obtained from the Sloan Kettering Mouse Genetics Core Facility, which were originally derived from the Jackson Labs NSG strain.

For biodistribution experiments, female Balb/c mice (n=3/group) were injected retroorbitally with either 3-arm 1-step, 4-arm 1-step, or 4-arm 2-step labeled $^{225}$Ac-HuM195 (11.1 kBq, 300 nCi). Injections were performed on a staggered schedule to prevent distortion of the results at early timepoints. At various times post-injection (t=2.5 hours; and 1, 3, 6, and 12-13 days), animals were euthanized and blood was collected via cardiac puncture. Organs were harvested, weighed, and separated into 12×75 test tubes. These tubes were counted on a Cobra II gamma counter (Packard) along with injected dose standards. Results were expressed as percent injected dose per gram of organ, with or without normalization to blood activity. A portion of blood was allowed to coagulate at 4 degrees Celsius overnight and was spun down at 16,100 g for 10 minutes to obtain serum. This was used in immunoreactivity and protein G binding assays as described below.

For therapy experiments, male NSG mice (n=5/group) were injected with 1e6 Set2-Luc cells intravenously via the lateral tail vein. On day 7 post-tumor injection, the animals were injected with D-luciferin potassium salt (Gold Biotechnology, 1 mg/mouse in 0.1 ml/mouse IV retroorbitally) and imaged on an IVIS 200 instrument (PerkinElmer). Images were analyzed by drawing regions of interest over the whole animal in Living Image software (PerkinElmer). Mice were divided into groups of 5 such that the average signal intensity was the same for each group. On day 10 post-tumor injection, animals were treated by injecting 0.555 kBq (15 nCi) or 1.11 kBq (30 nCi) of 3-arm $^{225}$Ac-HuM195, 3-arm $^{225}$Ac-Rituximab+unlabeled HuM195, 4-arm $^{225}$Ac-HuM195, 4-arm $^{225}$Ac-Rituximab+unlabeled HuM195, or vehicle control (1% HSA) retroorbitally. The protein amount of each antibody was at 0.225 mg regardless of the radioactive dose and was adjusted by adding the appropriate unlabeled construct. Bioluminescent imaging was carried out every 5-7 days thereafter, and the experiment was terminated after imaging on day 26, before overt morbidity from tumors was observed. All animal studies were approved by the Institutional Animal Care and Use Committee of MSKCC under protocol 96-11-044.

Quality Control of Radioimmunoconjugates

The percent of $^{225}$AC bound to the radioimmunoconjugates was determined by instant thin-layer chromatography using silica gel (iTLC-SG) paper (Agilent Technologies). The paper was cut into strips, and small aliquots of the radioimmunoconjugate were spotted onto these strips at Rf=0. The strips were then developed using two different mobile phases. Mobile phase I was 10 mM EDTA, and mobile phase II was 9% NaCl/10 mM NaOH. After development in mobile phase I, the Rf of the radiolabeled antibody was 0, and the Rf of both the free metal species and metal in unconjugated chelates was 1.0. After development in mobile phase II, the Rf of both the radiolabeled antibody and free metal species was 0, and the Rf of the metal chelates was 1.0. The strips were cut in the middle, and the halves were counted separately in a Cobra II gamma counter (Packard).

Immunoreactivity of the constructs radiolabeled with actinium-225 was determined using a cell-based assay with excess antigen as described previously (15). The positive cell line used was Set2-Luc, and the negative cell line was Ramos. Briefly, 10e6 cells per tube were first blocked with 1 ml of 2% human AB serum/1% bovine serum albumin in PBS for 20 min on ice. Cells were then pelleted, and to each pellet was added radiolabeled antibody (2 ng) in 20 μl of the blocking buffer. After a 40-minute incubation on ice, 100 μl of blocking buffer was added. The supernatant plus two washes were transferred to a scintillation vial, while the pellet was transferred to a second vial. ScintiSafe Gel (5 ml, Fisher Scientific) was added to each tube, and the tubes were counted on a Tri-Carb 2910 TR liquid scintillation analyzer (PerkinElmer) after equilibrium.

Protein G binding of the antibodies was determined by incubating serum extracted from treated mice (3 μl per sample) with protein G agarose (Thermo Scientific, 10 μL settled resin). It was assumed that the amount of radioimmunoconjugate was small compared to the total IgG in the serum, and the amount of protein G agarose was calculated such that all IgG in the sample should be bound. The remaining volume in the incubation was occupied by 1% HSA (17 μl) for a total of 30 μl per incubation. Samples were incubated at room temperature for 2 h, the supernatant and two washes were separated from the protein G pellet, and the radioactivity was measured on a beta scintillation counter as described for immunoreactivity.

Serum Stability In Vitro

Purified radioimmunoconjugates (0.1 ml) were added to 100% human AB serum (0.9 ml) in 1.8 ml Nunc tubes and incubated at 37 degrees Celsius. At various timepoints, an aliquot (30 ml) was removed from each sample and mixed with 50 mM DTPA (10 μl) to challenge off any metal that was not stably chelated to the antibody. After incubation of this aliquot at 37 degrees Celsius for 15 minutes, 8 ml was spotted in triplicate on iTLC strips and developed as described above.

Flow Cytometry Analysis

For cell surface staining, cells were incubated with appropriate mAbs for 30 min on ice, washed, and incubated with a R-phycoerythrin-labeled goat anti-rat secondary antibody. Flow cytometry data were collected on a FACSCalibur (Becton-Dickinson) or Accuri C6 (BD Biosciences) and analyzed with FlowJo version 10.0.6 software.

Statistical Analysis

Data were graphed using GraphPad Prism software (Graphpad Software Inc). Unless specifically noted, values reported represent means ±SD. Statistical comparisons between the experimental groups were performed either via the Student's t-test (two-group comparison) or via one-way ANOVA with Bonferroni's multiple comparison post-hoc test (multiple-group comparison). P values were calculated using GraphPad Prism, with P<0.05 considered significant.

Example 2

Formation of Antibody-Chelate Constructs

Figure 1B:
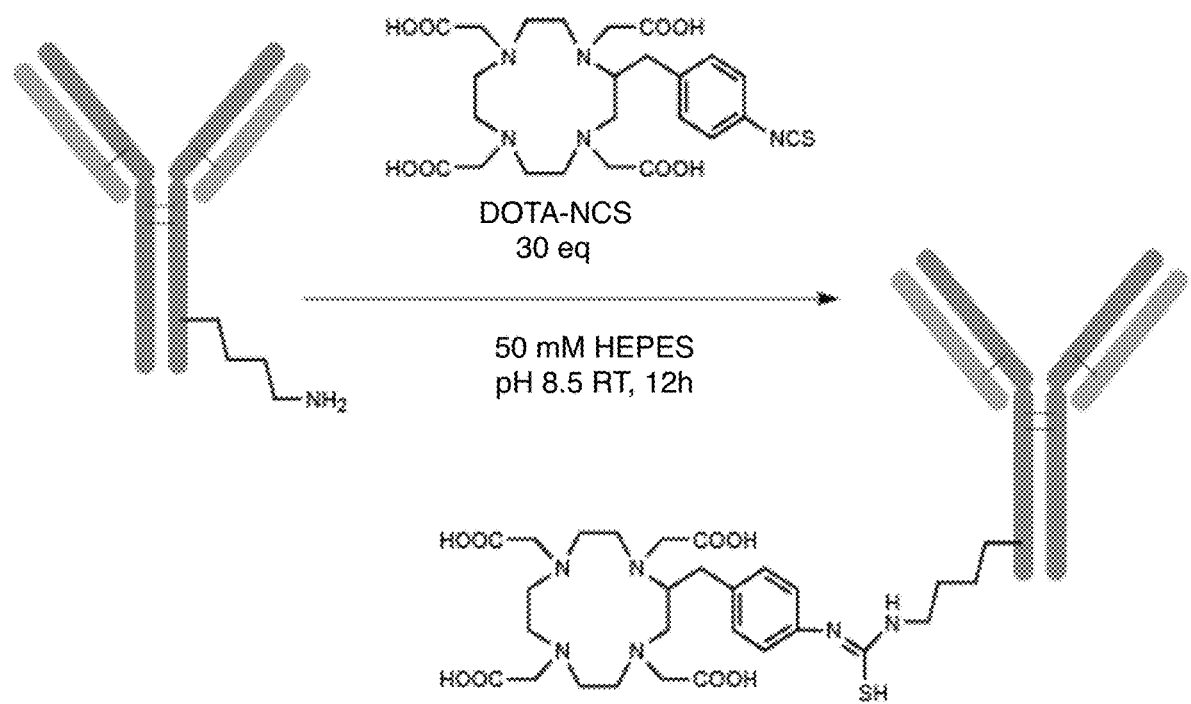

Constructs of antibodies attached to several different chelating moieties were generated using two attachment chemistries. These included "3-arm" DOTA constructs, in which one of the four carboxylic acids of DOTA is used to attach to antibody lysines via N-hydroxysuccinimide chemistry (FIG. 1A), and "4-arm" DOTA constructs in which a benzyl isothiocyanate group attaches to antibody lysines leaving all four carboxylic acids free (FIG. 1B). As controls, antibody constructs with DTPA, which previous reports indicated would not chelate $^{225}$AC at all[4]; and CHX-A"-DTPA, which was reported to chelate $^{225}$AC weakly during the labeling but release the metal upon serum challenge[3],

TABLE 1

Statistics on Conjugation of Antibody Constructs

| Antibody | Chelate (DOTA) | Abbreviated Name | Active Ester Used (eq) | Substitution amount (DOTA/Ab) | Scale |
|---|---|---|---|---|---|
| HuM195 | 3-arm | 3A-HuM | 15, 30, 60 | 4.5, 9.9*, 18.3 | 10 mg |
|  | 4-arm | 4A-HuM | 30, 40 | 10.3*, 13.1 | 5 mg |
| Rituximab | 3-arm | 3A-Rit | 60 | 9.5* | 5 mg |
|  | 4-arm | 4A-Rit | 30 | 9.8* | 5 mg |

Example 3

Figure 2A:
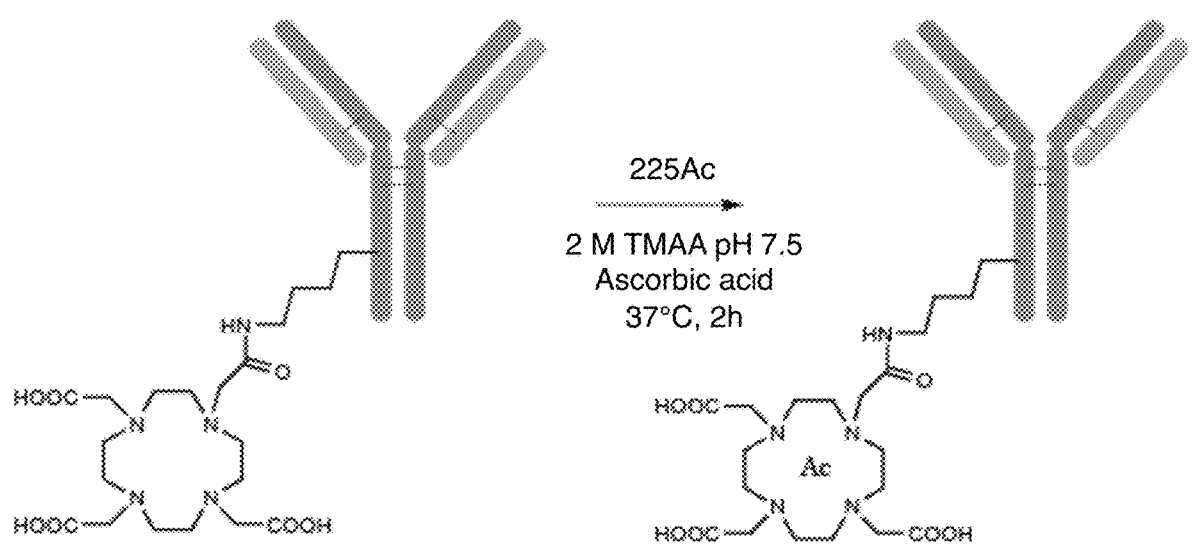
FIGS. 2A-2B illustrate that "3-arm" and "4-arm" constructs can be radiolabeled in one step at 37° Celsius.
Figure 2B:
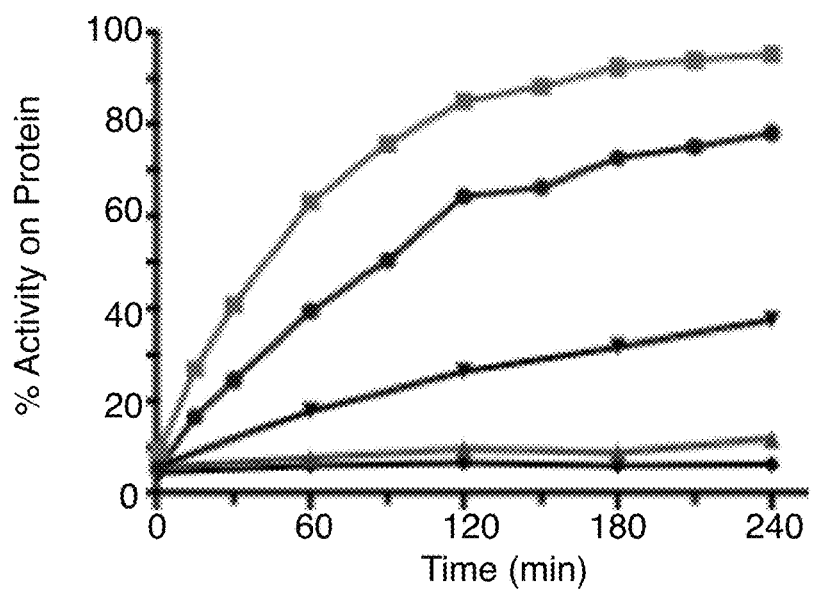

Radiolabeling, Quality Control, and Stability In Vitro 3-arm and 4-arm constructs were radiolabeled using conditions shown in FIG. 2A. The kinetics of labeling were determined through periodic iTLC of aliquots of the reactions (FIG. 2B). Surprisingly, the 4-arm construct appeared to radiolabel more quickly than the 3-arm construct, with approximately 95% of the activity incorporated onto protein after 4 hours as compared to only 78% for the 3-arm construct. Both constructs labeled more slowly at room temperature than at 37 degrees. Constructs were radiolabeled for 2 hours for future studies. At this timepoint, 85% of the actinium was incorporated onto the 4-arm construct and 64% was incorporated onto the 3-arm construct for specific activities of approximately 0.18 and 0.14 Ci/g protein, respectively.

In a separate experiment, constructs were radiolabeled to a range of specific activities using a 2 hour procedure (Table 2). Radiochemical purity of the products was good to excellent, except for the high-specific-activity 3A-HuM labeling which had too much free $^{225}$AC leftover to remove with the 10 DG column. The limit of specific activity that could be achieved with the 2 hour procedure was about 0.8 Ci/g for the 3-arm construct and about 3.5 Ci/g for the 4 arm construct. Immunoreactivity for both constructs decreased slightly as the amount of $^{225}$AC in the reaction increased. The sham-labeled construct showed a small amount of background accumulation (~7%) on both positive and negative cells.

TABLE 2

Data From Representative 2-hour Radiolabeling

Figure 1C:
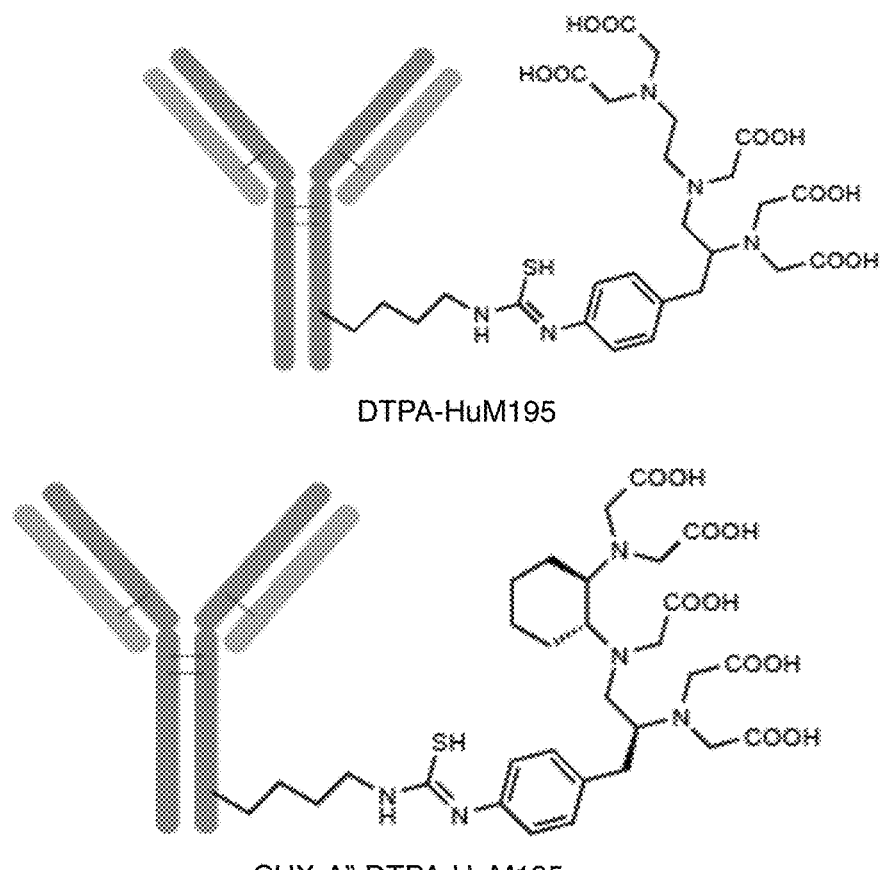

| Construct (0.1 mg) | 225Ac Added (μCi) | Activity on Purified Product (μCi) | Radiochem. Yield (%) | Radiochem. Purity by iTLC (%) | Specific Activity (Ci/g) | Approx #Ab per Ac-225 | Immunoreact. vs Set2-Luc (%) | Immunoreact vs Ramos (%) |
|---|---|---|---|---|---|---|---|---|
| 3A-HuM | 580 | 85.2 | 10.5 | 69.06 | 0.74 | 118 | 77 ± 3 | 0.09 ± 0.02 |
| 3A-HuM | 109 | 65.23 | 57.4 | 95.98 | 0.78 | 111 | 80 ± 1 | 0.09 ± 0.04 |
| 3A-HuM | 22.75 | 14.63 | 62.8 | 97.64 | 0.18 | 487 | 84 ± 1.5 | 0.1 ± 0.1 |
| 4A-HuM | 534.5 | 284 | 52.2 | 98.27 | 3.49 | 25 | 75.1 ± 0.6 | 0.14 ± 0.04 |
| 4A-HuM | 113 | 88.69 | 78.0 | 99.32 | 1.10 | 79 | 83 ± 1 | 0.08 ± 0.01 |
| 4A-HuM | 22.35 | 18.28 | 81.2 | 99.32 | 0.23 | 383 | 86 ± 1.5 | 0.13 ± 0.07 |
| Unmod-HuM | 105.5 | N/A | N/A | 11.61 | N/A | N/A | 7.6 ± 0.5 | 7 ± 5 | were generated (FIG. 1C). Antibodies were conjugated to two or more different substitution ratios, and constructs with about 10 DOTAs per antibody were used for future assays. Table 1 lists data on the conjugation of two representative antibodies, as well as abbreviated names that will be used throughout the rest of the text.

Figure 3A:
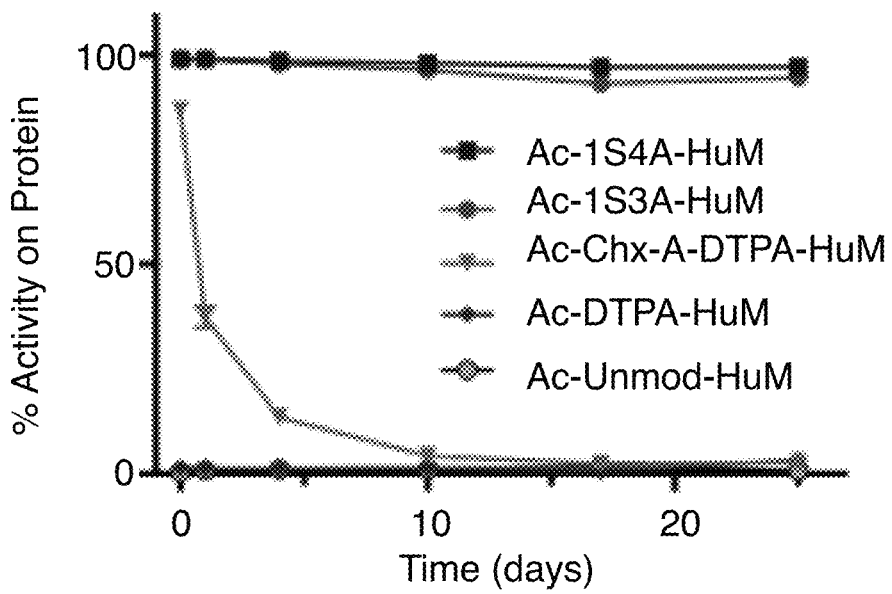
FIGS. 3A-3B show that "3-arm" and "4-arm" constructs labeled with one step are stable to serum challenge at 37° Celsius.

Radiolabeled 3-arm and 4-arm constructs and controls were exposed to 90% human serum at 37 degrees Celsius in vitro, challenged with excess DTPA to remove any weakly-bound $^{225}$AC, and assayed for actinium remaining on protein by iTLC (FIG. 3A). 95-97% of the $^{225}$AC remained on the constructs after 25 days. By contrast, $^{225}$AC from the unpurified reactions of DTPA construct and unmodified HuM195 did not appear to bind to protein strongly enough to overcome DTPA challenge at any timepoint. As expected, the CHX-A"-DTPA construct initially bound $^{225}$AC but then released it over time.

Example 4

Biodistribution and Stability In Vivo

Figure 3B:
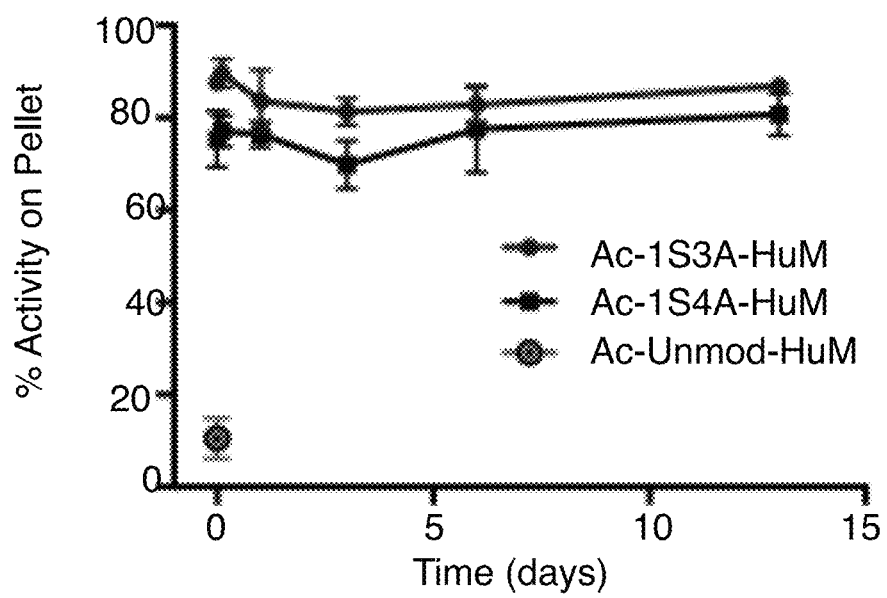

The radiolabeled 3-arm and 4-arm constructs were injected into healthy Balb/c mice to determine the constructs' serum stability in vivo and their tissue distribution as compared to the 4-arm 2-step labeled construct. Constructs harvested from serum at timepoints of up to 13 days showed nearly undiminished binding to Protein G sepharose beads as compared to uninjected material, while actinium-225 combined with unmodified HuM195 showed little binding to the beads (FIG. 3B). At day 13, 225Ac in the serum of animals treated with the 3-arm construct was 80±2% immunoreactive towards Set-2 Luc cells, while the corresponding number for the 4-arm construct was 81±2%.

Figure 4A:
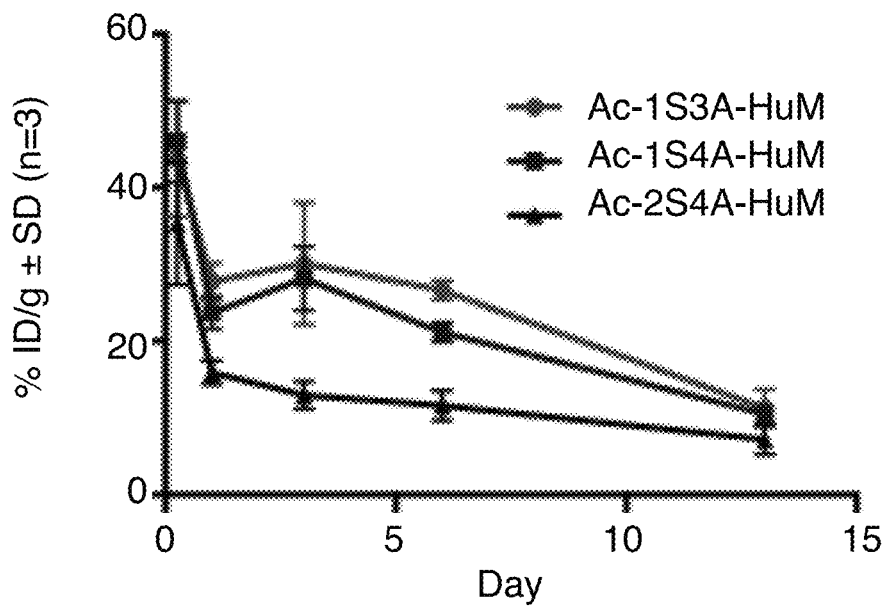
FIGS. 4A-4D show that tissue distribution of one-step labeled constructs as compared to 4-arm two-step construct in blood (FIG. 4A), bone plus marrow (FIG. 4B), liver (FIG. 4C), and liver normalized to blood (FIG. 4D).
Figure 4B:
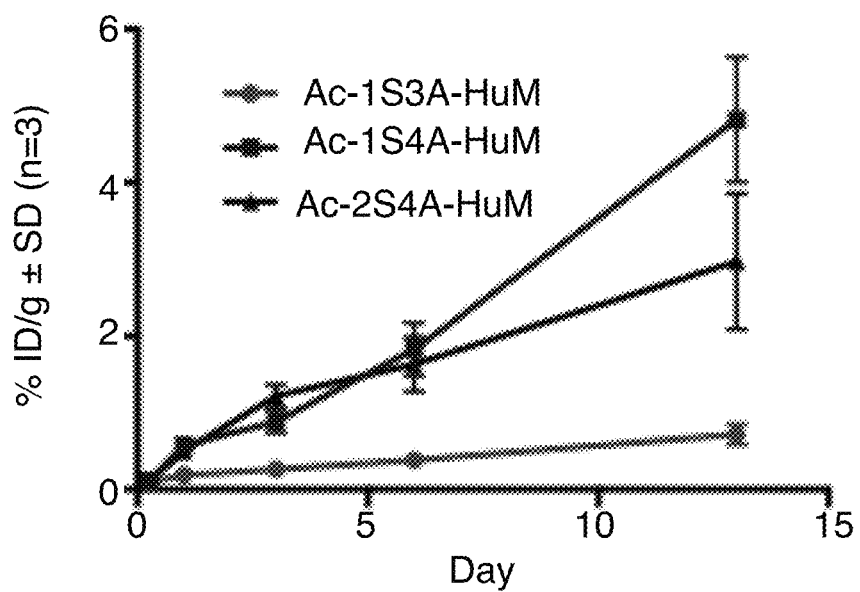
Figure 4C:
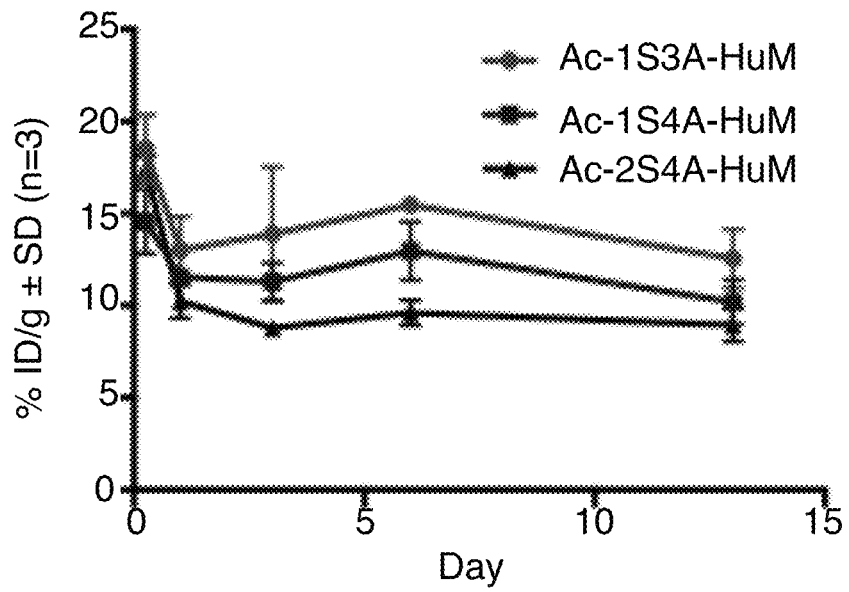
Figure 4D:
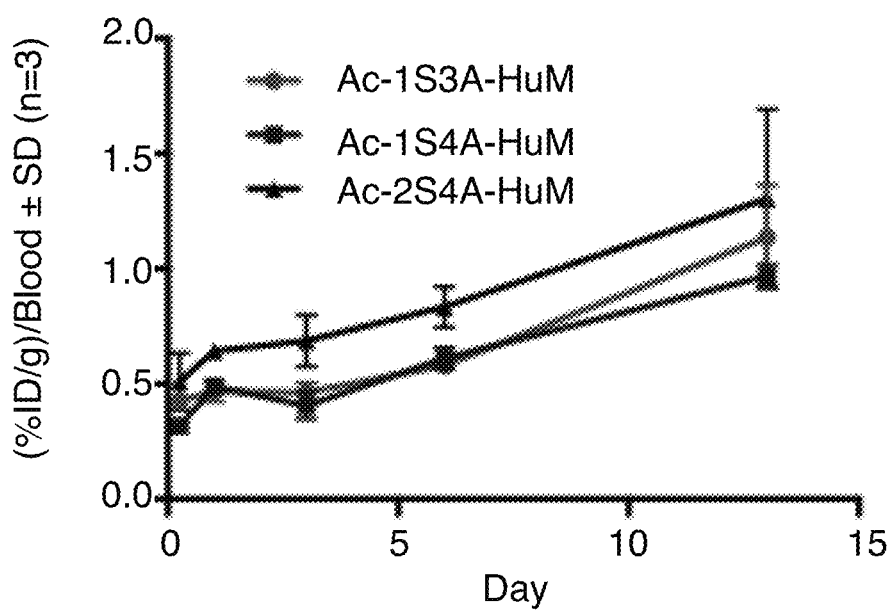
Figure 6A:
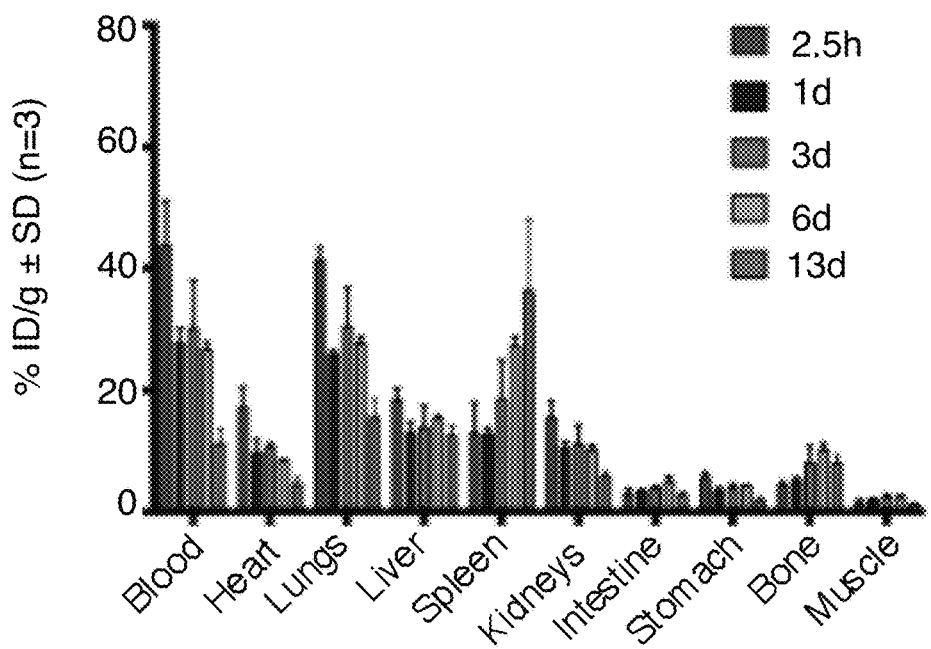
FIGS. 6A-6C show the biodistribution in female Balb/C mice of Ac-1S3A-HuM (FIG. 6A), Ac-1S4A-HuM (FIG. 6B) and Ac-2S4A-HuM (FIG. 6C).
Figure 6B:
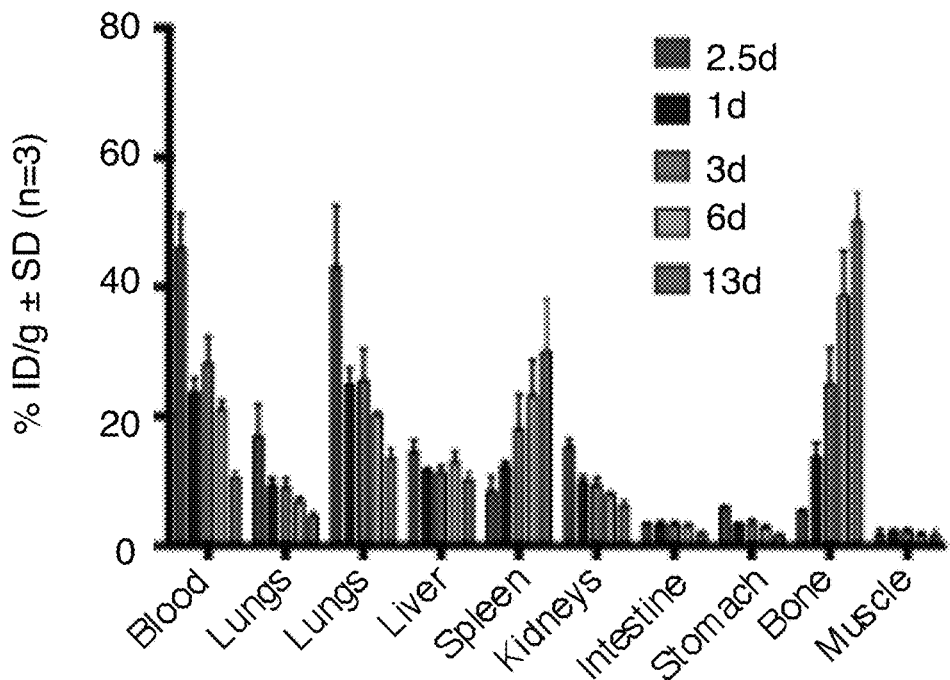
Figure 6C:
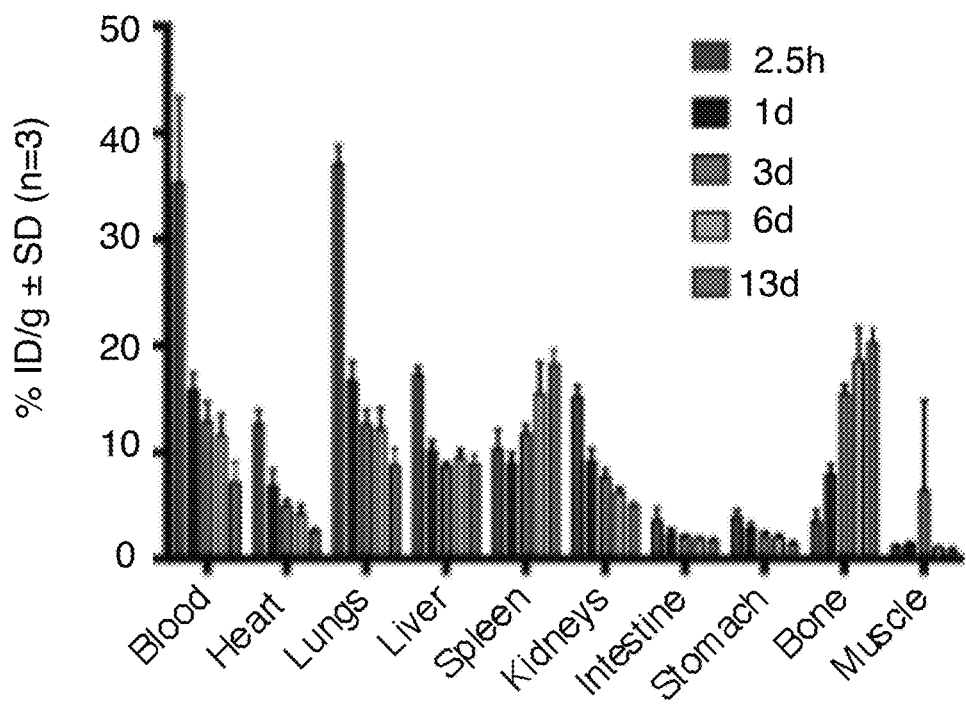

Biodistribution of the constructs indicated that the serum half-life of both 1-step constructs was significantly longer than that of the 2-step constructs (FIGS. 4A-4D). Radioactivity in many organs correlated with the blood values. When normalized to the blood, the three constructs showed similar accumulations in all organs except bone (including marrow), where the four-arm constructs labeled with both one and two steps had significantly higher accumulations than the three-arm construct (FIG. 4B). All three constructs produced a small and stable accumulation of radioactivity in the liver. All three constructs also had substantial increases in % injected dose per gram in the spleen over time, but this was due to transient decreases in spleen weight due to the relatively high dose of actinium-225 used, rather than a continued accumulation of activity. Complete graphs of the biodistribution of each construct are given as FIGS. 6A-6C. The results of this experiment were consistent with those of two other biodistributions performed comparing the 3-arm 1-step and 4-arm 2-step constructs.

Example 5

Therapy of Set-2 AML with HuM195

Figure 5A:
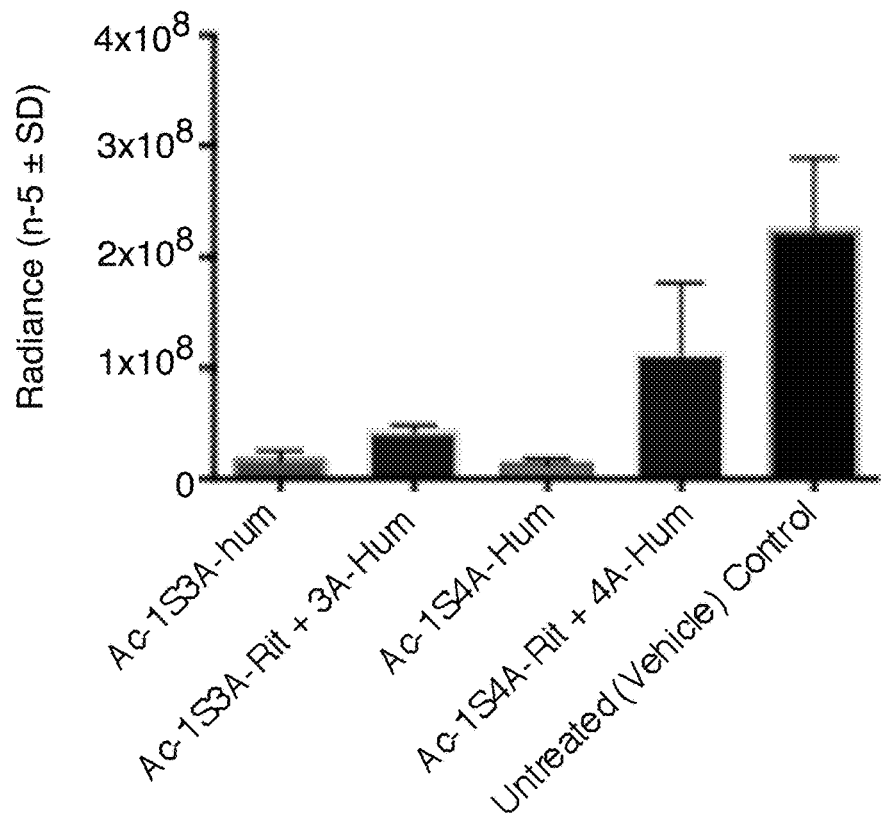
FIGS. 5A-5C show 225Ac-antibody therapy in mouse model of AML, as determined by bioluminescent intensity.
Figure 5B:
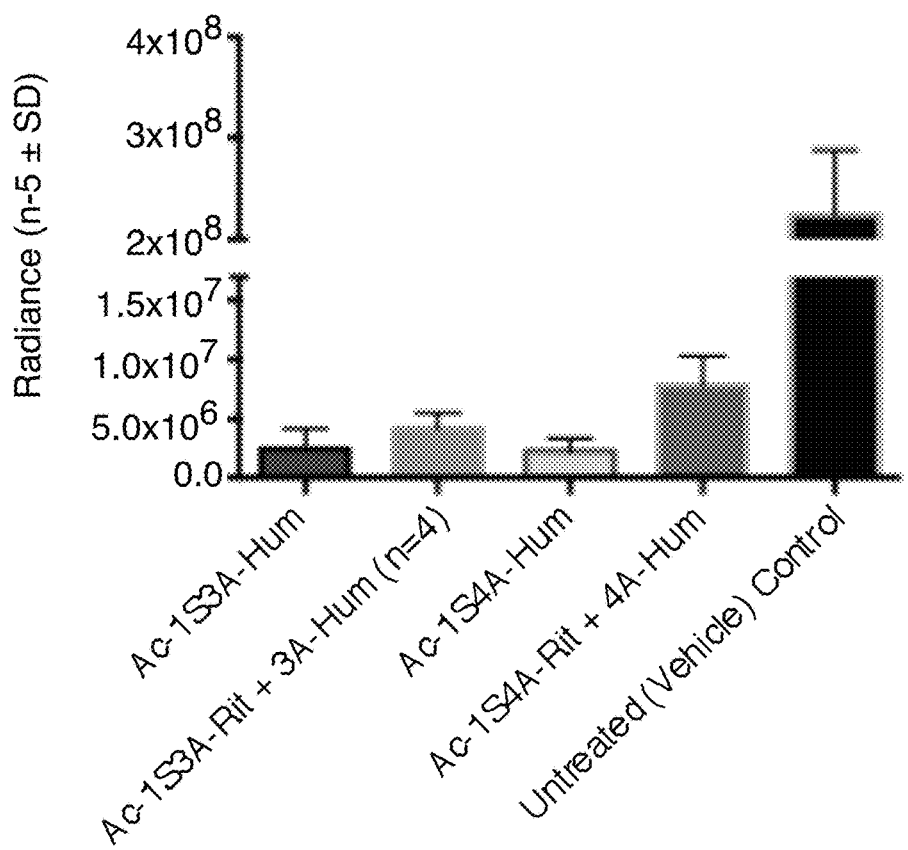
Figure 5C:
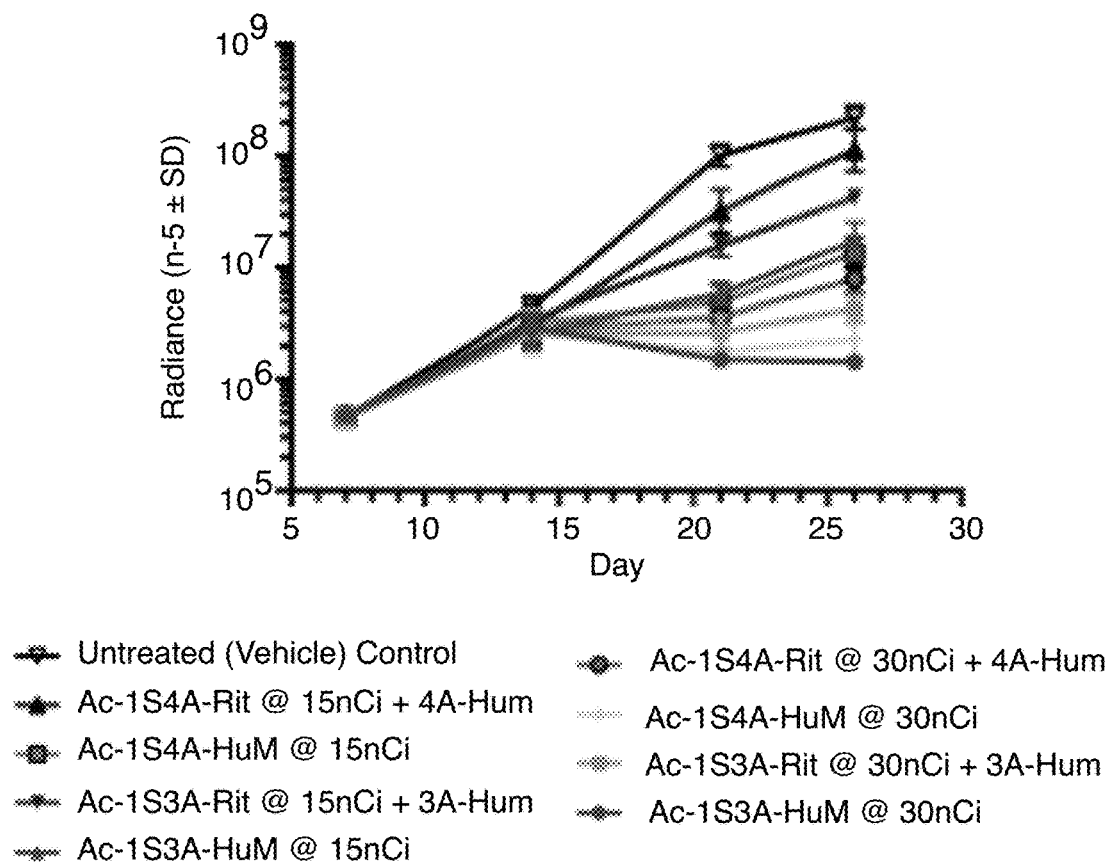
Figure 7:
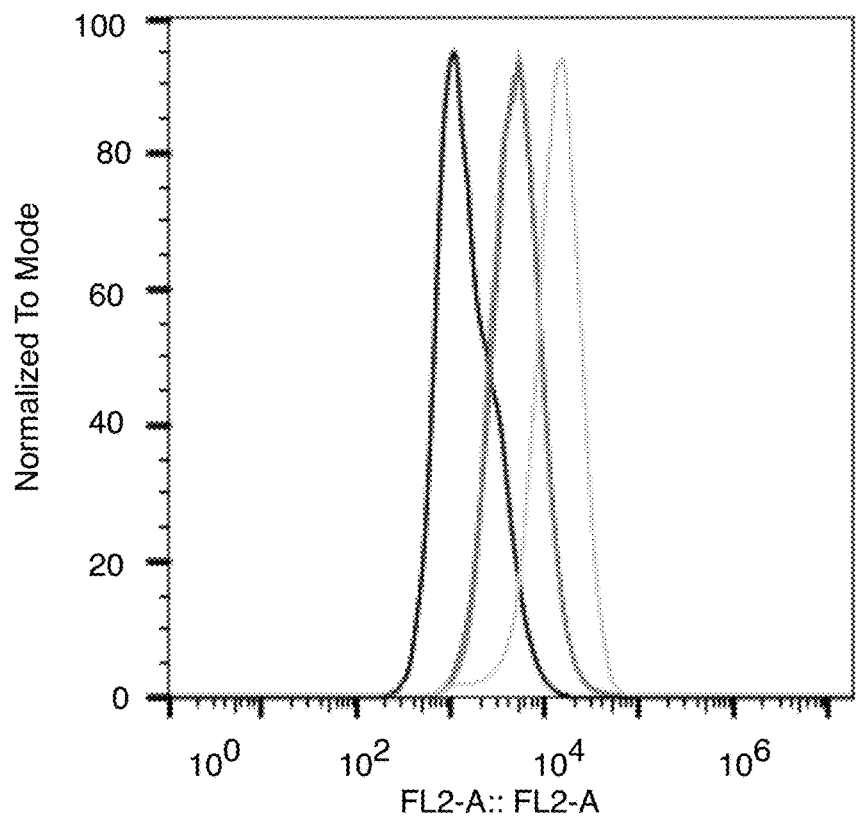
FIG. 7 shows that HuM 195 is immunoreactive towards Set2-Luc, while Rituximab is not.

The megakaryoblastic leukemia line Set-2 stably expressing luciferase (Set-2Luc) was determined to bind HuM195 but not rituximab by flow cytometry (FIG. 7). Male NSG mice (n=5/group) bearing disseminated disease with Set2-Luc cells were treated on day 10 post-tumor implantation with a single administration of $^{225}$Ac-labeled 3-arm and 4-arm constructs at either 15 or 30 nCi. One animal in the 3-arm 30 nCi dual control group died on day 17 (day 7 post-treatment), possibly from actinium-related toxicity. For all radiolabeled constructs, the 30 nCi dose produced approximately a ten-fold increased response over the 15 nCi dose of corresponding construct (FIGS. 5A-5B). The radiolabeled nonspecific antibody plus unlabeled specific construct produced significant responses over vehicle, but in every case the specific construct was substantially more effective than the nonspecific control. This was statistically significant in every case except the higher dose of 3-arm construct. The 30 nCi doses of both specific constructs caused reduction of tumor burden between days 14 and 26 (FIG. 5C). The experiment was terminated after imaging on day 26.

Example 6

Therapy of Set-2 with ESK

TABLE 3

Therapy scheme of Set2-Luc in NSG mice

| Group | Radioactive Dose | Specific Activity (Ci/g) | Total Protein (μg) | Injection |
|---|---|---|---|---|
| 1. Untreated (vehicle) | n/a (vehicle) | n/a (vehicle) | n/a (vehicle) | Once, Day 11 |
| 2. Cold ESK D2655A | n/a | n/a | 0.20 | Once, Day 11 |
| 3. Cold ESKM, 50 μg | n/a | n/a | 50 | Twice weekly, starting Day 11 |
| 4. Ac-Iso, 30 nCi | 30 nCi MGo53-mIgG1 D265A | 0.29 | 0.10 | Once, Day 11 |
| 5. Low SA Ac-ESK, 30 nCi | 30 nCi ESK-mIgG1 D265A | 0.029 | 1.0 | Once, Day 11 |
| 6. Ac-ESK, 30 nCi | 30 nCi ESK-mIgG1 D265A | 0.29 | 0.10 | Once Day 11 |
| 7. Ac-Iso, 60 nCi | 30 nCi MGo53-mIgG1 D265A | 0.29 | 0.20 | Once, Day 11 |
| 8. Ac-ESK, 60 nCi | 60 nCi ESK-mIgG1 D265A | 0.29 | 0.20 | Once, Day 11 |

Figure 8:
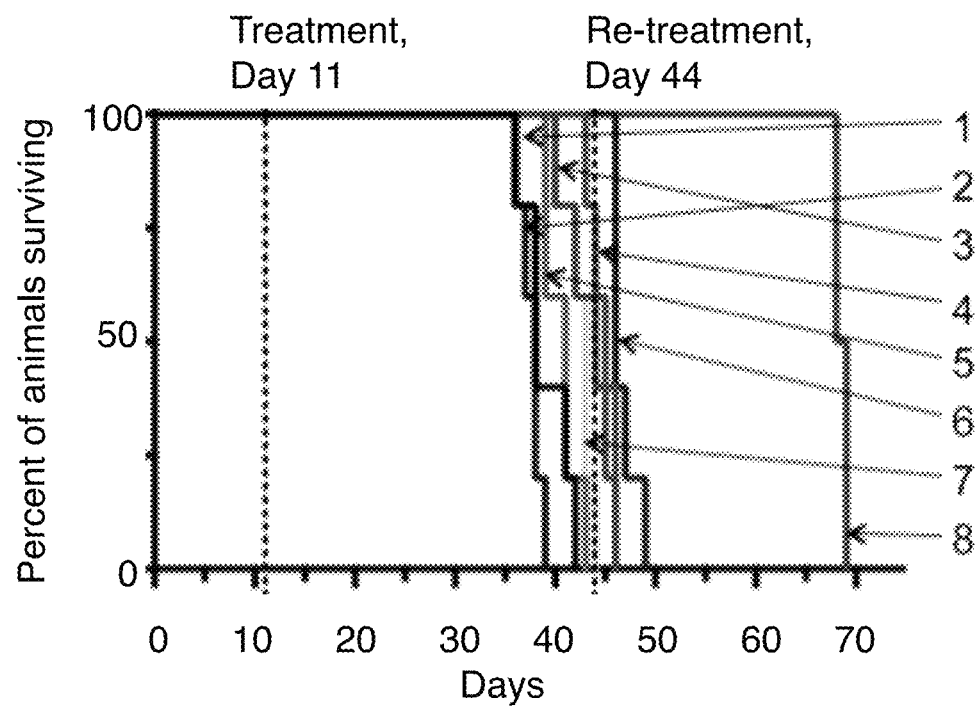
FIG. 8 shows survival curves for mice bearing Set2-Luc tumors treated as described in Table 3 with Ac225-ESK constructs.

NSG mice (n=5/group) bearing disseminated disease with megakaryblastic leukemia Set2-Luc cells were treated on day 11 post-tumor implantation according to the therapy schema of Table 3. The Ac225-Iso and Ac225-ESK constructs at 60 nCi were treated a second time on day 44. The animals were followed for survival endpoints. One animal in the Ac225-ESK at 60 nCi group died shortly after therapy, but this was deemed unrelated to actinium toxicity or leukemic burden. The 60 nCi dose of the Ac225-ESK of 0.2 ug antibody construct extended survival as compared to controls including mice treated with more than 500 ug of ESKM antibody (FIG. 8). Thus, the radiolabeled antibody has a more than 1000 times potency compared to that of non-radiolabeled antibody.

Example 7

Therapy of JMN with ESK

TABLE 4

Therapy scheme of JMN-Luc in CB17-SCID mice

| Group | Radioactive Dose | Specific Activity (Ci/g) | Total Protein (ug) | Injection |
|---|---|---|---|---|
| 1. Untreated (vehicle) | n/a (vehicle) | n/a (vehicle) | n/a (vehicle) | Once, Day 11 |
| 2. Cold ESK D2655A | n/a | n/a | 0.62 | Once, Day 11 |
| 3. Ac-Iso, 180 nCi | 180 nCi MGo53-mIgG1 D265A | 0.29 | 0.62 | Once, Day 11 |
| 4. Low SA Ac-ESK, 180 nCi | 180 nCi ESK-mIgG1 D265A | 0.029 | 6.2 | Once, Day 11 |
| 5. Ac-ESK, 180 nCi | 180 nCi ESK-mIgG1 D265A | 0.29 | 0.62 | Once, Day 11 |

Figure 9:
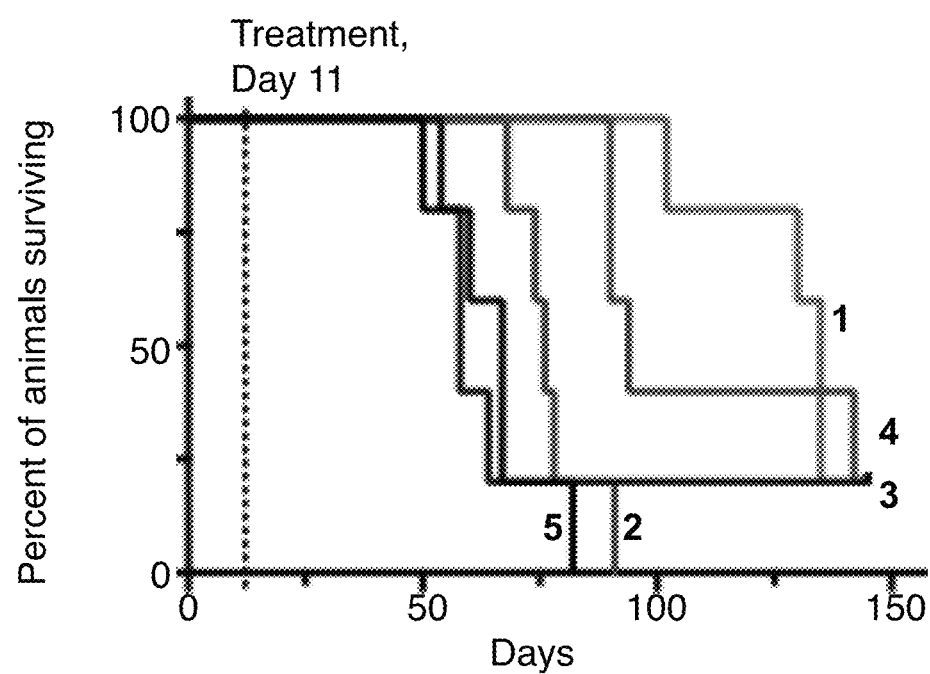
FIG. 9 shows survival curves for mice bearing JMN tumors treated as described in Table 4 with Ac225-ESK constructs. Marked prolongation of survival was seen in mice treated with 180 nCi of Ac-225 and 0.62 ug ESK antibody as compared to controls.

CB17-SCID mice (n=5/group) bearing disseminated disease with human mesothelioma JMN-Luc cells were treated on day 11 post-tumor implantation according to the therapy schema of Table 4. The animals were followed for survival endpoints. The 180 nCi dose of the Ac225-ESK of 0.62 ug antibody construct extended survival as compared to controls (FIG. 9). Thus, the radiolabeled antibody has a more than 1000 times potency compared to that of the non-radiolabeled antibody.

The following references were cited herein:
1. Kluetz et al., Clin Cancer Res Off J Am Assoc Cancer Res, 20:9-14, 2014.
2. Scheinberg et al., Curr Radiopharm, 4:306-320, 2011.
3. Davis et al., Nucl Med Biol, 26:581-589, 1999.
4. McDevitt et al., Appl Radiat Isot Data Instrum Methods Use Agric Ind Med, 57:841-847, 2002.
5. Kennel et al., Cancer Biother Radiopharm, 15:235-244, 2000.
6. McDevitt et al., Science, 294:1537-1540, 2001.
7. Escorcia et al., Cancer Res, 70:9277-9286, 2010.
8. Ballangrud et al., Clin Cancer Res Off J Am Assoc Cancer Res, 10:4489-4497, 2004.
9. Borchardt et al., Cancer Res, 63:5084-5090, 2003.
10. Miederer et al., Clin Cancer Res Off J Am Assoc Cancer Res, 14:3555-3561, 2008.
11. Essler et al., Eur J Nucl Med Mol Imaging, 39:602-612, 2012.
12. Smith-Jones et al., Cancer Res, 60:5237-5243, 2000.
13. Lewis et al., Bioconjug Chem, 12:320-324, 2001.
14. Dadachova et al., Nucl Med Biol, 26:977-982, 1999.
15. Sgouros et al., J Nucl Med, 51:311-328, 2010.
16. Nikula et al., J Nucl Med Off Publ Soc Nucl Med, 40:166-176, 1999.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A one-step chelation process for actinium-225, comprising:
chelating, at a physiological temperature of about 37° C. and a pH of about 5.8, actinium-225 to a 1,4,7,10-tetraazacyclododecane-1,4,7,10-tetraacetic acid (DOTA) comprising a bifunctional ligand conjugated thereto in a 3-arm configuration and a monoclonal antibody covalently linked thereto in a ratio of about 10 DOTAs per monoclonal antibody to produce an actinium-225-DOTA-monoclonal antibody complex chelated at a high specific activity of about 0.7 Ci/g to about 3.5 Ci/g.

2. The one-step chelation process of claim 1, wherein a radiochemical yield of said process is about 50% to about 85%.

3. The one-step chelation process of claim 1, wherein the bifunctional ligand is benzyl-isothiocyanate or N-hydroxysuccinimide.

4. A method for increasing the radiochemical yield of an actinium-225-DOTA-monoclonal antibody complex, comprising:
conjugating 1,4,7,10-tetraazacyclododecane-1,4,7,10-tetraacetic acid (DOTA) to a monoclonal antibody via a bifunctional ligand in a 3-arm configuration to form a DOTA-monoclonal antibody construct in a ratio of about 10 chelators per monoclonal antibody; and
chelating actinium-225 to said 3-arm DOTA-monoclonal antibody construct at a physiological temperature of about 37° C. and a pH of about 5.8 to form an actinium-225-DOTA-monoclonal antibody complex, said reaction enabling an increase in an amount of actinium-225 chelated thereto to a high specific activity of about 0.7 Ci/g to about 3.5 Ci/g, thereby increasing the radiochemical yield of the complex.

5. The method of claim 4, wherein said radiochemical yield is about 50% to about 85%.

6. A method for producing a high specific activity actinium-225-DOTA-monoclonal antibody complex, comprising:
chelating at a physiological temperature of about 37° C. and a pH of about 5.8 actinium-225 to a DOTA-monoclonal antibody construct that comprises about 10 DOTA per monoclonal antibody and a bifunctional ligand conjugating said monoclonal antibody to the DOTA in a 3-arm or a 4-arm configuration, said physiological temperature and pH enabling an increase in the activity incorporated onto the monoclonal antibody, thereby producing the high specific activity actinium-225 complex of about 0.7 Ci/g to about 3.5 Ci/g.

7. The method of claim 6, wherein a radiochemical yield of said complex is about 50% to about 85%.

8. The method of claim 6, wherein the bifunctional ligand is benzyl-isothiocyanate or N-hydroxysuccinimide.

9. An actinium-225-DOTA-monoclonal antibody complex in a 4-arm configuration with the high-specific activity of about 0.7 Ci/g to about 3.5 Ci/g produced by the method of claim 6 or a pharmaceutical composition thereof.

* * * * *